United States Patent [19]
Back et al.

[11] Patent Number: 5,702,411
[45] Date of Patent: Dec. 30, 1997

[54] CLAMPING RING FOR A SURGICAL CLIP

[75] Inventors: Lothar Back, Inzighofen; Gebhard Herrmann, Irndorf; Markus Nesper, Tuttlingen; Dieter Weisshaupt, Immendingen, all of Germany

[73] Assignee: Aesculap AG, Tuttlingen, Germany

[21] Appl. No.: 700,009

[22] Filed: Aug. 20, 1996

[30] Foreign Application Priority Data

Sep. 15, 1995 [DE] Germany ............... 195 34 323.9

[51] Int. Cl.$^6$ ............................................. A61B 17/08
[52] U.S. Cl. .................................... 606/157; 60/158
[58] Field of Search ........................... 606/151, 157, 606/158, 142, 143, 139; 24/543, 545, 546, 536, 537, 541

[56] References Cited

U.S. PATENT DOCUMENTS

| | | |
|---|---|---|
| 4,794,927 | 1/1989 | Yoon ............................ 128/326 |
| 5,366,459 | 11/1994 | Yoon ............................ 606/151 |
| 5,445,167 | 8/1995 | Yoon et al. . |
| 5,520,701 | 5/1996 | Lerch ........................... 606/142 |

FOREIGN PATENT DOCUMENTS 43 19 829  8/1994  Germany .

*Primary Examiner*—Michael Buiz
*Assistant Examiner*—Tina T. D. Pham
*Attorney, Agent, or Firm*—Barry R. Lipsitz; Ralph F. Hoppin

[57] ABSTRACT

To enable easier manufacturability of the clamping ring for a surgical clip comprising two arms which are elastically pivotable towards each other and each have one clamping jaw, an end section in which the arms meet, and located therebetween a tensioning section on which the clamping ring surrounding the arms is displaceable in the longitudinal direction, with a part connected to the clamping ring engaging between the arms, it is proposed that the clamping ring carry diametrically opposed projections integrally formed on the clamping ring and protruding inwardly into the area surrounded by the clamping ring.

27 Claims, 2 Drawing Sheets

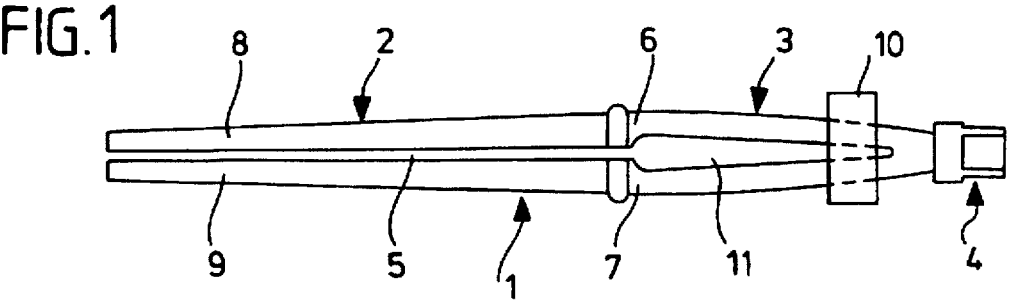
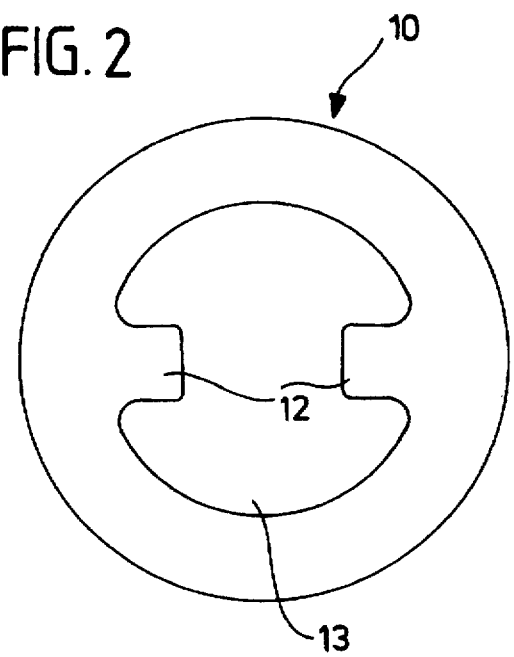
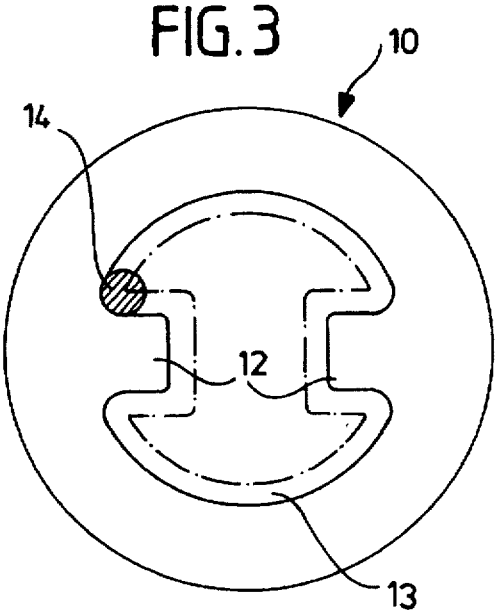
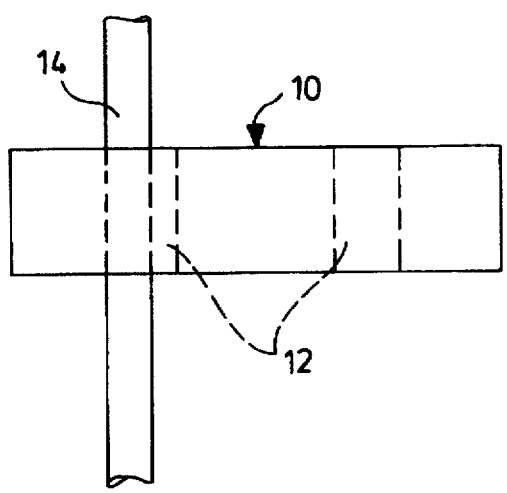

CLAMPING RING FOR A SURGICAL CLIP

BACKGROUND OF THE INVENTION

The invention relates to a clamping ring for a surgical clip comprising two arms which are elastically pivotable towards each other and each have one clamping jaw, an end section in which the arms meet, and located therebetween a tensioning section on which the clamping ring surrounding the arms is displaceable in the longitudinal direction, with a part connected to the clamping ring engaging between the arms.

Such a surgical clip is known, for example, from DE 43 19 829 C1. It can be applied and released again with the aid of a special applicator. In order to spread out the clip after application, provision is made in the known clip for the clamping ring to carry a pin extending radially through the clamping ring. The pin engages between the arms and spreads these open when the clamping ring is pushed back.

The clamping ring is a part with extremely small dimensions, and it is, therefore, very difficult to manufacture such a ring with a separate pin extending through it, particularly since the pin also protrudes on both sides of the known clamping ring on the outside thereof.

The object of the invention is to manufacture a clamping ring for a generic clip in a simple way.

SUMMARY OF THE INVENTION

This object is accomplished in accordance with the invention with a clamping ring of the generic kind by the clamping ring carrying diametrically opposed projections integrally formed on the clamping ring and protruding inwardly into the area surrounded by the clamping ring.

Accordingly, a pin engaging between the arms and having to be connected to the clamping ring is no longer used, but instead the clamping ring itself carries on both sides thereof inwardly protruding projections which engage between the arms and spread these open when the clamping ring is pushed back.

The projections can be in the form of radial webs, the length of which preferably corresponds at most to half the radius of the area enclosed by the clamping ring.

The inner contour of the area adjacent to the projections and enclosed by the clamping ring may differ in design. It is preferably adapted to the outer contour of the arms of the clip. For example, this inner contour can be a circular arc or an elliptical section.

The outer contour of the clamping ring may also differ in design. For example, the clamping ring can be circular or elliptical.

In a modified embodiment of the clamping rings provision is made for the clamping ring to carry diametrically opposed projections which are integrally formed on the clamping ring and protrude outwardly.

With a suitable tool it is possible to grip the clamping ring at these outwardly protruding projections and thereby displace the clamping ring in a direction transverse to the plane thereof. The clip on which the clamping ring is arranged can thereby be moved from the closed position to the open position and vice versa.

It is expedient for the projections protruding inwardly into the clamping ring and the projections protruding outwardly from the clamping ring to lie on a diameter line of the clamping ring. This results in application at both sides of the clamping ring in the region of the projections engaging inwardly between the arms of the tissue clip. The forces are, therefore, applied symmetrically and jamming is thereby virtually excluded.

Provision may be made for the length of the outwardly protruding projections to correspond at most to half the radius of the area enclosed by the clamping ring.

The outwardly protruding projections may preferably be in the form of radial webs.

It is particularly expedient for the inwardly and/or outwardly protruding projections to have the same height as the clamping ring and for the flat end faces of the clamping ring to also delimit the projections. These flat end faces are thus also flat side faces of the inwardly and/or outwardly protruding projections, which, therefore, have an essentially rectangular cross section.

However, provision may also be made in another embodiment for the outwardly protruding projections to have a circular-cylindrical shape. Herein it is, in particular, expedient for the diameter of the circular-cylindrical, outwardly protruding projections to be smaller than the thickness of the clamping ring.

The manufacture of a clamping ring, which constitutes a very small component, can be carried out in accordance with a preferred embodiment of the invention by the clamping ring being made from a disk by means of a wire eroding machine. With the latter it is possible to machine an inner recess with an optional contour in such a disk.

In a similar way, instead of a wire eroding machine, an electron beam device or a laser beam device can be used, possibly also a water jet device. With these devices an inner recess with the corresponding contour is cut in the disk in the same way as with the wire eroding machine.

In a modified embodiment provision may also be made for the clamping ring to be a ceramic shaped body. Such an embodiment is expedient particularly when there are circular-cylindrical, outwardly protruding projections provided on the clamping ring which cannot be readily cut out of a disk with a wire eroding machine or with other beam devices.

The following description of preferred embodiments of the invention serves in conjunction with the appended drawings to explain the invention in greater detail.

BRIEF DESCRIPTION OF THE DRAWINGS

FIG. 1 a schematic view of a surgical clip with a clamping ring displaceable thereon;

FIG. 2 a plan view of a clamping ring made of ceramics with inwardly formed projections;

FIG. 3 a plan view of a clamping ring with inwardly projecting radial webs and the wire of a wire eroding machine when the inner recess of the clamping ring is being made;

FIG. 4 a side view of the clamping ring of FIG. 3 with the wire of a wire eroding machine;

DETAILED DESCRIPTION OF THE INVENTION

Figure 5:
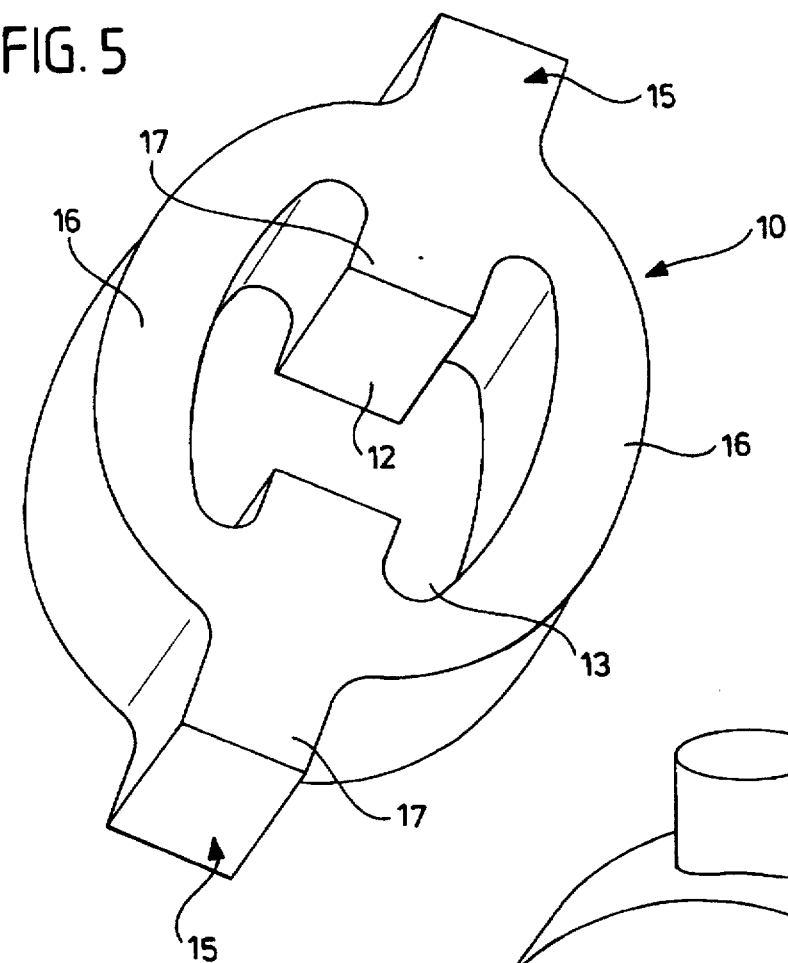
FIG. 5 a perspective view of a further preferred embodiment of a clamping ring with outwardly protruding projections of rectangular cross section.

The surgical clip 1 illustrated in FIG. 1 comprises a clamping section 2, a tensioning section 3 and an end section 4 one behind the other in the longitudinal direction thereof.

Over the major part of its length the clip 1 is divided by a longitudinal slot 5 into two arms 6, 7 which meet in the end section 4.

These two arms 6, 7 form two clamping jaws 8, 9 arranged opposite each other in the clamping section 2. In the tensioning section 3, the arms 6, 7 widen conically from the end section 4 to the clamping jaws 8, 9, and in this region the arms 6, 7 are surrounded by a clamping ring 10 which is displaceable in the longitudinal direction on the arms 6, 7 in the tensioning section 3. When the clamping ring 10 is pushed forward, it presses the arms 6, 7 together elastically and thereby clamps the clamping jaws 8, 9 of the clip 1 against each other.

The longitudinal slot 5 widens in the region of the tensioning section 3 into a wedge-shaped space 11 which tapers towards the end section 4. Projections 12 which are integrally formed on the clamping ring 10 and project inwardly therefrom (FIGS. 2 and 3) engage in this space 11. These projections 12 are preferably formed by radial webs, the length of which corresponds approximately to half the radius of the area 13 enclosed by the clamping ring 10.

The contour of the enclosed area 13 in the part adjacent to the projections 12 can have the shape of a circular arc, but another shape can also be chosen, for example, the shape of an elliptical arc. In particular, this contour is adapted to the outer contour of the arms 6, 7 of the clip 1.

In the embodiment of FIGS. 2 and 3, the clamping ring has only inwardly directed projections 12. On the outer side thereof, the clamping ring is of circular design.

In the modified embodiment illustrated in FIG. 5, which in other respects corresponds to the embodiments of FIGS. 2 and 3, and in which identical parts, therefore, also have identical reference numerals, two radially outwardly protruding projections 15 are additionally provided. The projections 15 are arranged directly opposite to the inwardly protruding projections 12, i.e., a common diameter line of the clamping ring runs through all inwardly and outwardly protruding projections 12 and 15, respectively. The inwardly protruding projections 12 and the outwardly protruding projections 15 are of rectangular cross section. The flat end face 16 on opposite sides of the clamping ring continues into the side faces 17 of these projections 12 and 15, respectively, i.e., the clamping rings are delimited in the entire region thereof by these flat end faces 16.

Figure 6:
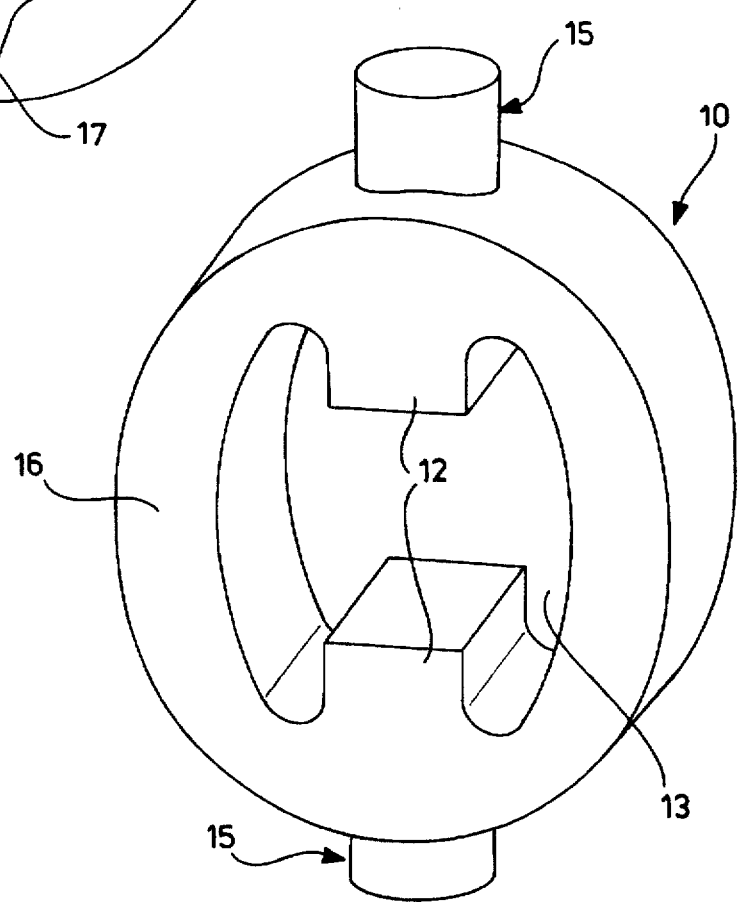
FIG. 6 a view similar to FIG. 5 with outwardly protruding projections of circular-cylindrical cross section.

In the embodiment of FIG. 6, on the other hand, the outwardly protruding projections 15 are of circular-cylindrical design, and the diameter of these circular cylinders is smaller than the thickness of the clamping ring 10.

In both cases, the outwardly protruding projections 15 serve as areas for the application of a tool with which the clamping ring can be displaced in a direction transverse to its plane on the clip 1. To this end, the outwardly protruding projections 15 extend into corresponding recesses of a tool, as is known per se with clamping rings which carry continuous pins (DE 43 19 829 C1).

The clamping ring 10 can, for example, be produced as a shaped part from ceramics, as illustrated in FIG. 2. This type of production is particularly advantageous when outwardly protruding, circular-cylindrical projections 15 are formed on the clamping ring, as illustrated in FIG. 6.

However, it can also be in the form of a metal part, in which case it is advantageous for the manufacture of the clamping ring 10 to start from a disk-shaped body consisting of metal, out of which an area 13 of essentially circular shape is cut by means of a wire eroding machine, with the inwardly protruding projections 12 extending into this circular area. The area actually cut out is thus essentially H-shaped, as is apparent from FIG. 3. To cut out this H-shaped recess, the wire 14 of a wire eroding machine is guided along the contour of this cut-out area.

What is claimed is:

1. A clamping ring for a surgical clip, said clip comprising two arms which extend in a longitudinal direction and which are elastically pivotable.

2. A clamping ring as defined in claim 1, wherein:
said projections are in the form of radial webs.

3. A clamping ring as defined in claim 2, wherein
said area surrounded by said clamping ring has an associated radius; and
respective lengths of said projections are no greater than half said associated radius such that a gap is defined between said projections.

4. A clamping ring as defined in claim 1, wherein:
the inner contour of said area adjacent to said projections and enclosed by said clamping ring is a circular arc.

5. A clamping ring as defined in claim 1, wherein:
the inner contour of said area adjacent to said projections and enclosed by said clamping ring is an elliptical section.

6. A clamping ring as defined in claim 1, wherein:
an outer contour of said clamping ring is circular.

7. A clamping ring as defined in claim 1, wherein:
an outer contour of said clamping ring is elliptical.

8. A clamping ring as defined in claim 1, further comprising:
diametrically opposed projections integrally formed on said clamping ring and protruding outwardly.

9. A clamping ring as defined in claim 8, wherein:
said projections protruding inwardly and said projections protruding outwardly lie on a diameter line of said clamping ring.

10. A clamping ring as defined in claim 8, wherein:
said area surrounded by said clamping ring has an associated radius; and
respective lengths of said outwardly protruding projections are no greater than half said associated radius.

11. A clamping ring as defined in claim 9, wherein:
said area surrounded by said clamping ring has an associated radius; and
respective lengths of said outwardly protruding projections are no greater than half said associated radius.

12. A clamping ring as defined in claim 8, wherein:
said outwardly protruding projections are in the form of radial webs.

13. A clamping ring as defined in claim 8, wherein:
said inwardly and/or outwardly protruding projections and said clamping ring have the same height and substantially coplanar flat end faces.

14. A clamping ring as defined in claim 9, wherein:
said inwardly and/or outwardly protruding projections and said clamping ring have the same height and substantially coplanar flat end faces.

15. A clamping ring as defined in claim 8, wherein:
said outwardly protruding projections have a circular-cylindrical shape.

16. A clamping ring as defined in claim 15, wherein:
a diameter of said circular-cylindrical, outwardly protruding projections is smaller than a thickness of said clamping ring.

17. A clamping ring as defined in claim 1, wherein:

said inner contour is wire-eroded.
18. A clamping ring as defined in claim 8, wherein: said inner contour is wire-eroded.
19. A clamping ring as defined in claim 9, wherein: said inner contour is wire-eroded.
20. A clamping ring as defined in claim 1, wherein: said inner contour is electron beam or laser beam eroded.
21. A clamping ring as defined in claim 8, wherein: said inner contour is electron beam or laser beam eroded.
22. A clamping ring as defined in claim 9, wherein: said inner contour is electron beam or laser beam eroded.
23. A clamping ring as defined in claim 1, wherein: said ring is a shaped ceramic body.
24. A clamping ring as defined in claim 8, wherein: said ring is a shaded ceramic body.
25. A clamping ring as defined in claim 9, wherein: said ring is a shaped ceramic body.
26. A clamping ring for a surgical clip, said clip comprising two arms which extend in a longitudinal direction and which are elastically pivotable towards each other and each have one clamping jaw, an end section in which said arms meet, and a tensioning section located between said clamping jaws and said end section, said clamping ring surrounding said arms and being displaceable along said tensioning region in the longitudinal direction, said clamping ring comprising:

diametrically opposed projections formed in one piece with said clamping ring and protruding inwardly toward one another into an area surrounded by said clamping ring to engage between said arms; and diametrically opposed projections integrally formed on said clamping ring and protruding outwardly.

27. A clamping ring as defined in claim 26, wherein: said projections protruding inwardly and said projections protruding outwardly lie on a diameter line of said clamping ring.

\* \* \* \* \*

UNITED STATES PATENT AND TRADEMARK OFFICE
CERTIFICATE OF CORRECTION

PATENT NO. : 5,702,411
DATED : Dec. 30, 1997
INVENTOR(S) : Back et al.

It is certified that error appears in the above-identified patent and that said Letters Patent is hereby corrected as shown below:

Claim 1 is revised to read: --A clamping ring for a surgical clip, said clip comprising two arms which extend in a longitudinal direction and which are elastically pivotable towards each other and each have one clamping jaw, an end section in which said arms meet, and a tensioning section located between said clamping jaws and said end section, said clamping ring surrounding said arms and being displaceable along said tensioning region in the longitudinal direction, said clamping ring comprising:

diametrically opposed projections formed in one piece with said clamping ring and protruding inwardly toward one another into an area surrounded by said clamping ring;

said projections being located between said arms and being adapted to spread said arms apart when the clamping ring is displaced toward the end section of the surgical clip.--

Column 5, line 1: "said" is changed to --an--; line 3: "said" is changed to --an--; line 5: "said" is changed to --an--; line 7: "said" is changed to --an--; line 9: "said" is changed to --an--; line 11: "said" is changed to --an--; line 15: "shaded" is changed to --shaped--.

Signed and Sealed this

Twenty-sixth Day of May, 1998

*Attest:*

BRUCE LEHMAN

*Attesting Officer*       *Commissioner of Patents and Trademarks*